United States Patent [19]

Pawlowski et al.

[11] Patent Number: 5,716,756
[45] Date of Patent: Feb. 10, 1998

[54] SULFONIC ACID ESTERS, RADIATION-SENSITIVE MIXTURES PREPARED THEREWITH AND THEIR USE

[75] Inventors: Georg Pawlowski, Tokyo, Japan; Walter Spiess, Muenster, Germany; Horst Roeschert, Ober-Hilbersheim, Germany; Wolfgang Appel, Kelkheim, Germany; Walter Herr, Eppstein, Germany

[73] Assignees: Hoechst Aktiengesellschaft, Frankfurt; Herberts GmbH, Wuppertal, both of Germany

[21] Appl. No.: 424,532

[22] PCT Filed: Oct. 4, 1993

[86] PCT No.: PCT/EP93/02701

§ 371 Date: May 30, 1995

§ 102(e) Date: May 30, 1995

[87] PCT Pub. No.: WO94/18606

PCT Pub. Date: Aug. 18, 1994

[30] Foreign Application Priority Data

Feb. 1, 1993 [DE] Germany .................. 43 02 681.8

[51] Int. Cl.$^6$ .................. G03F 7/039; G03F 7/038; C07C 309/63
[52] U.S. Cl. .................. 430/270.1; 430/288.1; 430/280.1; 522/52; 522/53; 522/59; 546/136; 546/134; 558/46; 558/47; 552/211; 548/157; 548/169; 548/165
[58] Field of Search .................. 548/157, 169, 548/165; 552/211; 558/46, 47; 546/136, 134; 430/270.1, 280.1, 288.1; 522/52, 53, 59

[56] References Cited

U.S. PATENT DOCUMENTS

| | | |
|---|---|---|
| 3,732,273 | 5/1973 | Heine et al. .................. 260/456 R |
| 3,890,147 | 6/1975 | Monahan .................. 430/270.1 |
| 4,504,372 | 3/1985 | Kirchmayr et al. .................. 522/53 |
| 5,227,276 | 7/1993 | Roeschert et al. .................. 430/252 |
| 5,286,867 | 2/1994 | Lohaus et al. .................. 546/249 |
| 5,346,806 | 9/1994 | Pawlowski et al. .................. 430/284 |

FOREIGN PATENT DOCUMENTS 0 330 386  8/1989  European Pat. Off. .
0 388 343 A2  9/1990  European Pat. Off. .
0 497 342 A2  8/1992  European Pat. Off. .
0 510 444 A1  10/1992  European Pat. Off. .
0 510 447 A2  10/1992  European Pat. Off. .
41 12 967  10/1992  Germany .
3-223864  10/1991  Japan .

OTHER PUBLICATIONS

Ueno et al., "Chemical Amplification Positive Resist Systems Using Novel Sulfonates As Acid Generators", *Science and Technology*, pp. 66–67, (1989) No Month Given.

Astrologes et al., "Reactions Of Trialkoxysulfuranes (Ortho-sulfinates) With Trifluoromethanesulfonic Acid", *Journal of the American Chemical Society*, vol. 99:4400–4404, (1977) June.

Reynolds et al., "Exploring The Chemistry Of The 2-Arthexafluoro-2-Propanol Group", *J. Org. Chem.*, vol. 55(11):4448–4454, (1990) July.

Allen et al., "Doubly Destabilized Carbocations. Strong Aryl Delocalization And The Attenuation of Rate Decelerating Effects of $CF_3$ and CN Groups", *J. Am. Chem. Soc.*, vol. 108:3470–3474, (1986) June.

*Primary Examiner*—Cynthia Hamilton
*Attorney, Agent, or Firm*—Foley & Lardner

[57] ABSTRACT

Sulfonic acid esters are used as (a) compounds for forming a strong acid on irradiation in radiation-sensitive, positive or negative working mixtures also comprising (b) either a compound with at least one acid-decomposable C—O—C or C—O—Si bond (for positive working mixtures) or a compound with at least acid-cross-linkable groups (for negative working mixtures) and c) a binder which is insoluble in water but soluble or at least swellable in aqueous alkaline solutions, wherein said sulfonic acid esters are formula

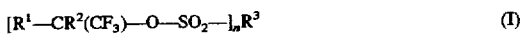

or

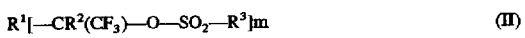

wherein $R^1$, $R^2$, $R^3$, n and n are defined with the body of the disclosure. These mixtures are particularly suitable for exposure to deep UV radiation in the formation of recording materials suitable for the production of photoresists, electronic components, and printing plates.

17 Claims, No Drawings

SULFONIC ACID ESTERS, RADIATION-SENSITIVE MIXTURES PREPARED THEREWITH AND THEIR USE

The invention relates to sulfonic acid esters and radiation-sensitive, positive-working or negative-working mixtures prepared therewith and comprising a) a compound forming a strong acid on irradiation, b) either a compound having at least one acid-cleavable C—O—C or C—O—Si bond (for a positive-working mixture) or a compound having at least two acid-crosslinkable groups (for a negative-working mixture) and c) a binder which is insoluble in water but soluble or at least swellable in aqueous alkaline solutions.

The invention furthermore relates to radiation-sensitive recording materials which are produced therefrom and which are suitable for the production of photoresists, electronic components and printing plates or for chemical milling.

Radiation-sensitive mixtures containing sulfonic acid esters as acid formers are particularly suitable for exposure to "deep-UV" radiation having a wavelength of 220 to 300 nm, in particular of 248 nm (KrF excimer lasers emit at this wavelength). Sulfonates of substituted phenols (JP-A 03-223 864) or of hydroxymethylbenzoins (DE-A 19 19 678), 2-nitrobenzylsulfonates (EP-A 0 330 386), pyrogallolsulfonates (T. Ueno et al. in "Polymers for Microelectronics— Science and Technology", Ed. Y. Tabata et al., Kodansha-Weinheim-New York, 1989, pages 66–67), N-sulfonyloxyimides (EP-A 0 388 343) or 1-sulfonyloxypyridones (DE-A 41 12 967) have been used to date as sulfonic acid esters. The disadvantages of these compounds are an excessively high intrinsic absorption in the DUV range, insufficient sensitivity (owing to too low a quantum yield in the acid-forming reaction) or insufficient solubility. This leads to deficiencies in the quality of image reproduction, to low throughput speeds of the wafers to be structured or to separation problems.

Many positive-working photoresist layers also contain compounds having acid-clearable groups in addition to the acid-forming aromatic sulfonic acid esters. If such layers are exposed imagewise, it is found that the line width obtained after development is influenced by the storage time between irradiation and heating step (post-exposure bake) and deviations from the original thus occur. The irradiation dose must therefore be adapted to the storage time. This dependence of the image quality on the storage time is a major technical problem which has not been solved to date. It presumably has a plurality of causes. Thus, it is assumed that photolysis products which are unstable and react in an undesirable manner during the storage time are formed from many of the acid-forming compounds used to date. In addition, relatively long storage times frequently lead to the formation of insoluble top layers whose prolonged development times lead to complications with the substantial automation of semiconductor production.

It was therefore the object of the invention to provide a radiation-sensitive mixture which has high sensitivity in particular to DUV radiation and at the same time high resolution down to the region of less than 500 nm. Regardless of the storage time between imagewise exposure and post-exposure bake, it should be simple to process and combine high process stability and processing range with accurate reproducibility and reliability.

The object is achieved by the provision of a radiation-sensitive, positive-working or negative-working mixture comprising a) a compound forming a strong acid on irradiation, b) either a compound having at least one acid-cleavable C—O—C or C—O—Si bond (for a positive-working mixture) or a compound having at least two acid-crosslinkable groups (for a negative-working mixture) and c) a binder which is insoluble in water but soluble or at least swellable in aqueous alkaline solutions, wherein the compound a) is a sulfonic acid ester of the formula

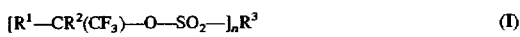

$$[R^1-CR^2(CF_3)-O-SO_2-]_n R^3 \qquad (I)$$

or

$$R^1[-CR^2(CF_3)-O-SO_2-R^3]_m \qquad (II)$$

in which $R^1$ in the compounds of the formula I is a mononuclear or polynuclear unfused or fused ($C_6$–$C_{14}$)aryl or ($C_4$–$C_{11}$) heteroaryl radical containing oxygen, sulfur or nitrogen as a heteroatom and in the compounds of the formula II is a divalent or trivalent radical of a mononuclear or polynuclear unfused or fused ($C_6$–$C_{14}$)aromatic or ($C_4$–$C_{12}$)heteroaromatic containing oxygen, sulfur or nitrogen as a heteroatom or a divalent radical of the formula —$C_6H_4$13 X—$C_6H_4$—, in which X is an oxygen atom, a carbonyl or sulfonyl group or a group $CR^7R^8$, in which $R^7$ and $R^8$ are identical or different and are a methyl or trifluoromethyl radical, is a hydrogen atom or a methyl, trifluoromethyl or cyano radical, in the compounds of the formula I where n=1 and in the compounds of the formula II is a straight-chain or branched, unsubstituted or substituted ($C_1$–$C_{18}$)alkyl radical, a ($C_4$–$C_{10}$)cycloalkyl radical, a ($C_2$–$C_6$)alkenyl radical, an unsubstituted or substituted ($C_6$–$C_{14}$)aryl or ($C_4$–$C_{12}$)heteroaryl radical containing oxygen, sulfur or nitrogen as a heteroatom or a ($C_7$–$C_{18}$)aralkyl radical and, in the compounds of the formula I where n=2 or 3, is a divalent or trivalent radical of a straight-chain or branched, unsubstituted or substituted ($C_1$–$C_{18}$)alkane or cycloalkane, of a mononuclear or polynuclear ($C_6$–$C_{14}$)-aromatic or of a ($C_4$–$C_{12}$)heteroaromatic containing oxygen, sulfur or nitrogen as a heteroatom, n is an integer from 1 to 3 and m is 2 or 3.

In the compounds of the formula I, the radical $R^1$ is preferably a phenyl, naphthyl, thiophen-2-yl, thiophen-3-yl, benzo[b]thiophen-2-yl or benzo[b]thiophen-3-yl or a phenyl radical to which a five- or six-membered ring having 1 to 3 heteroatoms, such as oxygen, nitrogen or sulfur, is fused, preferably a chromanyl, chromenyl, thiochromanyl, isochromanyl or isothiochromanyl, indolin-yl, benzothiazolyl, quinolyl, 1,2,3,4-tetrahydroquinolyl or isoquinolyl radical. It may be substituted by one to three identical or different substituents, such as fluorine, chlorine or bromine atoms, ($C_1$–$C_6$)alkyl, ($C_2$–$C_6$)alkenyl, ($C_2$–$C_4$)alkynyl, ($C_1$–$C_6$) alkoxy, ($C_6$–$C_{10}$)aryl, ($C_6$–$C_{10}$)aryloxy, ($C_7$–$C_{14}$)aralkyl, ($C_7$–$C_{14}$)aryloxyalkyl, ($C_7$–$C_{14}$)aryloxyalkoxy, ($C_1$–$C_6$) alkylthio, ($C_6$–$C_{10}$)arylthio, di($C_1$–$C_4$)alkylamino, ($C_1$–$C_6$) carboxyalkyl, cyano, nitro, ($C_1$–$C_{10}$)alkanesulfonyl or ($C_6$–$C_{14}$)arylsulfonyl groups or the groups $R^3$—$SO_2$—O—, $R^3$—$SO_2$—NH—, HO—$CR^2(CF_3)$— or $R^3$—$SO_2$—O— $CR^2(CF_3)$—, $R^2$ and $R^3$ being the monovalent radicals described above.

Preferred divalent radicals $R^1$ are meta- and para-phenylene. A preferred unfused divalent radical is biphenyl- 4,4'-diyl and a preferred fused radical is naphthalene-1,4-diyl. Among the radicals of the formula —$C_6H_4$—X—$C_6H_4$—, oxybiphenyl-4,4'-diyl is preferred. The polyvalent radicals $R^1$ may be substituted in the same manner as the monovalent ones.

$R^2$ is preferably a trifluoromethyl radical.

In the compounds of the formula I where n=1 and in the compounds of the formula II, $R^3$ is preferably a ($C_1$–$C_6$) alkyl radical, such as methyl, ethyl, propyl, isopropyl or butyl, a cycloalkyl radical, such as cyclohexyl, a perfluorinated or highly fluorinated ($C_1$–$C_6$)alkyl radical, such as trifluoromethyl, a ($C_6$–$C_{10}$)aryl radical, such as phenyl, tolyl, naphthyl, dihydronaphthyl or tetrahydronaphthyl, a ($C_7$–$C_{14}$)aralkyl radical, such as benzyl, or a ($C_4$–$C_9$) heteroaryl radical, such as thiophen-2-yl or thiophen-3-yl. In the compounds of the formula II where n=2, $R^3$ is preferably a ($C_1$–$C_{10}$)alkylene, in particular methylene, ethane-1,2-diyl or propane-1,3-diyl, or a ($C_6C_{10}$)arylene, in particular meta- or para-phenylene or naphthalenediyl. The radicals $R^3$ may be substituted in the same manner as the radicals $R^1$. Compounds in which the radical $R^3$ contain more than 15 carbon atoms give acids which exhibit even less diffusion, but these compounds have lower sensitivity to radiation.

The compounds of the formulae I and II can be prepared, for example, by reacting aliphatic or aromatic sulfonyl chlorides with unsubstituted or substituted 1-aryl-2,2,2-trifluoroethanol or 2-aryl-1,1,1-trifluoropropan-2-ol. The reaction is generally carried out in a solvent, such as tetrahydrofuran, methylene chloride or preferably dimethylformamide (DMF) in the presence of a base, such as triethylamine, pyridine or preferably sodium hydride. The fluorinated 1-arylethanols and 2-arylpropan-2-ols used as starting materials are obtainable by processes which are generally known to a person skilled in the art. 2-Aryl-1,1,1,3,3,3-hexafluoropropan-2-ol can be prepared, for example, by reacting an activated aromatic with hexafluoroacetone. Aromatics having lower activity react with hexafluoroacetone in the presence of small amounts of Lewis acid catalysts, preferably aluminum trichloride. Furthermore, Grignard compounds, prepared, for example, from brominated or iodinated aromatics, can be reacted with hexafluoroacetone to give the desired starting materials.

Only a few compounds of the formulae I and II are known. Thus, G. W. Astrologes and J. C. Martin (J. Amer. Chem. Soc. 99 [1977] 4400–4404) disclose compounds of the abovementioned formula I in which n=1, $R^1$=phenyl or 4-tert-butylphenyl and $R^2$=$R^3$=$CF_3$. D. W. Reynolds et al. (J. Org. Chem. 55 [1990] 4448–4454) disclose a compound of the formula II in which m=2, $R^1$=—$C_6H_3(CH_3)$—$C(CF_3)_2$—$C_6H_3(CH_3)$, $R^2$=$CF_3$ and $R^3$=$CH_3$. In the article by A. D. Allen et al. (J. Amer. Chem. Soc. 108 [1986] 3470–3474), further compounds of the formula I in which n=1, $R^1$=phenyl, 4-fluorophenyl, 4-methoxyphenyl or p-tolyl, $R^2$=$CF_3$ and $R^3$=p-tolyl and compounds in which n=1, $R^1$=phenyl or p-tolyl, $R^2$=CN and $R^3$=p-tolyl are described. The kinetics of the solvolysis of these compounds in different solvents was investigated. On the other hand, the compounds of the formula I in which n=2 or 3 and the compounds of the formula II, with the exception of the one known compound, are novel and form part of the invention. The use of compounds of the formula I or II as photosensitive acid generators in a radiation-sensitive mixture is novel and forms part of the present invention. The finding that the radiation-sensitivity of these sulfonic acid esters is as a rule several times higher than that of the known sulfonic acid esters was surprising. Particularly surprising, however, was the observation that these compounds make it possible to produce a radiation-sensitive layer in which the latent image formed after imagewise exposure is substantially stabilized.

The radicals $R^1$ and $R^3$ in the compounds of the general formulae I and II have only little effect on the efficiency of acid formation whereas a strongly electro-negative substituent $R^2$ increases the efficiency. Compounds which contain the —$C(CF_3)_2$—O—$SO_2$ radical as the structural element are therefore also particularly suitable acid formers. For reasons which are not clear, compounds which contain two or more radicals of this type are particularly efficient acid formers. Surprisingly, it is precisely these compounds which also have good thermal stability and sufficient stability to solvolysis, so that the compounds and the mixtures prepared therewith can be stored for a relatively long time without changing. The layers produced using the mixtures according to the invention, in particular the positive-working mixtures, have substantially better properties than layers comprising known mixtures. Undesirable effects, such as, for example, the change in the line widths, in the sensitivity or in the material removal rates during different storage times between exposure and post-exposure bake, occur to a substantially smaller extent.

In the mixture according to the invention, different acid-forming compounds of the formulae I and/or II may also be combined.

Combinations with photolytic acid donors used to date, for example onium salts, such as diazonium, phosphonium, sulfonium and iodonium salts of nonnucleophilic acids, for example of $HSbF_6$, $HAsF_6$ or $HPF_6$, halogen compounds, in particular trichloromethyltriazine derivatives or trichloromethyloxadiazole derivatives, o-quinonediazidesulfonyl chlorides or combinations of organometallic compounds and organohalogen compounds are also possible, but the above-mentioned disadvantages once again occur to a pronounced extent.

The amount of compounds of the general formulae I and/or II in the mixture according to the invention is in general 0.5 to 25% by weight, preferably 1 to 10% by weight, based in each case on the total weight of the solids in the mixture.

In addition to the photosensitive acid generators of the general formula I or II, the mixtures according to the invention contain an acid-sensitive compound and a film-forming polymer. Depending on the type of acid-sensitive compound, the mixture according to the invention may be positive-working or negative-working. In the case of positive-working materials, mixtures having acid-cleavable solubility inhibitors are preferred.

In particular, the following have proven suitable as acid-cleavable material in the radiation-sensitive mixture according to the invention:

a) Compounds having at least one orthocarboxylic ester and/or carboxamidoacetal group, it being possible for the compounds also to have polymeric character and for the stated groups to occur as linking elements in the main chain or as pendant substituents, b) oligomeric or polymeric compounds having repeating acetal and/or ketal groups in the main chain, c) compounds having at least one enol ether or N-acyliminocarbonate group, d) cyclic acetals or ketals of β-ketoesters or -amides, e) compounds having silylether groups, f) compounds having silyl-enol ether groups, g) monoacetals or monoketals whose aldehyde or ketone component has a solubility in the developer of from 0.1 to 100 g/l, h) ethers based on tertiary alcohols, i) carboxylic esters and carbonates whose alcohol component is a tertiary alcohol, an allyl alcohol or a benzyl alcohol, j) N,O-acetals, in particular N,O-polyacetals.

Mixtures of the stated acid-cleavable materials may also be used, although this is less preferable. Among the stated acid-cleavable materials, those having C—O—C bonds are preferred. Materials which are of the types (a), (b), (g), (i) and (j) are particularly preferred. Under type (b), the polymeric acetals are to be singled out; among the acid-cleavable materials of type (g), in particular those whose aldehyde or ketone component has a boiling point greater than 150° C., preferably greater than 200° C. However, the N,O-acetals of the type (j) are very particularly preferred.

The amount of acid-cleavable compounds in the radiation-sensitive mixture according to the invention should be 1 to 50% by weight, preferably 5 to 40% by weight, based in each case on the total weight of the solids.

For a negative-working mixture, suitable acid-crosslinkable compounds are resols and aromatics, heterocycles and monomeric or oligomeric melamine/formaldehyde or urea/formaldehyde condensates, which are each poly-substituted by hydroxymethyl, alkoxymethyl, in particular methoxymethyl, acetoxymethyl or glycidyl. Examples of suitable resols are in particular the commercially available (®)Bakelite R 5363, R 17620 and R 10282 and (®)Kelrez 40-152. In the deep UV range, resol derivatives result in relatively high absorptions which may adversely affect image reproductions and are therefore not preferred.

The known crosslinking agents of the general formula III

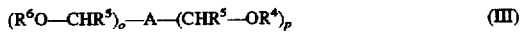

$(R^6O—CHR^5)_o—A—(CHR^5—OR^4)_p$      (III)

in which

A is —B— or —B—Y—B— and

B is the divalent radical of an unsubstituted or substituted mononuclear aromatic hydrocarbon or of an oxygen- or sulfur-containing heterocyclic aromatic compound, Y is a single bond, $(C_1-C_4)$alkylene or $(C_1-C_4)$—alkylenedioxy whose chains may be interrupted by oxygen atoms, or is —O—, —S—, —$SO_2$—, —CO—, —$CO_2$—, —O—$CO_2$—, —CO—NH— or phenylenedioxy, $R^4$ and $R^6$ are hydrogen, $(C_1-C_6)$alkyl, $C_5$— or $C_6$—cycloalkyl, unsubstituted or substituted $(C_6-C_{12})$ aryl, $(C_6-C_{12})$aralkyl or acyl, $R^5$ is hydrogen, $(C_1-C_4)$alkyl or unsubstituted or substituted phenyl, o is an integer from 1 to 3 and p is an integer from 0 to 3, the sum o+p being at least 2 are suitable.

Finally, low molecular weight or oligomeric silanols may also be used as crosslinking agents. Examples of these are dimethylsilanediols or diphenylsilanediols or pre-condensed oligomers containing these units.

The crosslinking agents are capable of crosslinking with the polymers described below at elevated temperatures under the influence of the photolytically produced acid; they can form a carbonium cation under the conditions described above.

The amount of acid-crosslinkable compounds in the radiation-sensitive mixture according to the invention is 1 to 50% by weight, preferably 5 to 40% by weight, based in each case on the total weight of the solid components of the mixture.

The mixtures according to the invention furthermore contain at least one polymeric binder which is insoluble in water but soluble or at least swellable in aqueous alkaline solutions. The binder readily dissolves the other components of the mixtures according to the invention and has as low a self-absorption as possible, i.e. high transparency, in particular in the wavelength range from 190 to 300 nm.

Owing to their high self-absorption in the stated wavelength range, novolak condensation resins can therefore be used only together with other, more highly transparent binders. The mixing ratios depend predominantly on the type of binder to be mixed with the novolak resin. In general, the binder of the radiation-sensitive mixture according to the invention may contain up to 30% by weight, in particular up to 20% by weight, of a novolak condensation resin.

Suitable binders are homo- or copolymers of 4-hydroxystyrene and of its alkyl derivatives, for example of 3-methyl-4-hydroxystyrene or of 2,3- or 3,5-dimethyl-4-hydroxystyrene, and homo- or copolymers of other polyvinylphenols, for example of 3-hydroxystyrene, or acrylates or acrylamides which have phenolic hydroxy groups. Polymerizable compounds, such as styrene, methacrylic acid/methacrylate, acrylic acid/methacrylate or the like, may be used as comonomers in the copolymer.

Mixtures having a high plasma stability are obtained when silicon-containing vinyl monomers, for example vinyltrimethylsilane, are used for the preparation of copolymers of the above type. The transparency of these binders is in general even higher in the range of interest, so that improved structuring is possible.

Homo- or copolymers of maleimide may also be used with the same success. These binders, too, have high transparency in the wavelength range described. Here too, styrene, substituted styrenes, vinyl ethers, vinyl esters, vinylsilanyl compounds or (meth)acrylates are preferably used as comonomers.

Finally, copolymers of styrene with comonomers which result in an increase in solubility in aqueous alkaline solutions may also be used. These include, for example, maleic anhydride and maleic half-esters.

Provided that the optical qualities of the mixtures according to the invention are not adversely affected, combinations of the stated binders are possible in the mixture according to the invention but are not preferred.

The extinction of the binder or of the combination of binders for radiation of wavelength 248 nm is preferably less than 0.35 $\mu m^{-1}$, particularly preferably less than 0.25 $\mu m^{-1}$.

The glass transition temperature of the binder or of the combination of binders is advantageously at least 120° C.

The amount of binder is in general 1 to 95% by weight, preferably 5 to 90% by weight, particularly preferably 30 to 85% by weight, based in each case on the total weight of the solid components of the radiation-sensitive mixture.

In order to meet specific requirements, such as flexibility, adhesion and gloss, substances such as polyglycols, cellulose derivatives, such as ethylcellulose, dyes, pigments, plasticizers, wetting agents and leveling agents may also be added to the radiation-sensitive mixtures according to the invention.

Finally, the present invention also relates to a recording material having a substrate and a radiation-sensitive layer comprising the mixture according to the invention. The recording material is usually produced by coating the substrate with a solution of this mixture.

Suitable solvents for this purpose are in particular ethylene glycol, glycol ethers (such as glycol monomethyl ether, glycol dimethyl ether and glycol monoethyl ether), propylene glycol monoalkyl ethers (such as propylene glycol monomethyl ether), aliphatic esters (such as ethyl acetate, hydroxyethyl acetate, alkoxyethyl acetate, n-butyl acetate and amyl acetate), propylene glycol monoalkyl ether acetates (such as propylene glycol methyl ether acetate), ethers (such as tetrahydrofuran and dioxane), ketones (such as methyl ethyl ketone, methyl isobutyl ketone, cyclopentanone and cyclohexanone), DMF, dimethylacetamide, hexamethylphosphorotriamide, N-methylpyrrolidone and butyrolactone and any mixtures thereof. Glycol ethers, aliphatic esters and ketones are particularly preferred.

Finally, the choice of the solvent or solvent mixture depends on the coating method used, on the desired layer thickness and on the drying conditions. Furthermore, the solvents must be chemically neutral, i.e. they may not undergo irreversible reactions with the other components of the layer.

The solutions used for coating have, as a rule, a solids content of 5 to 60% by weight, preferably 10 to 50% by weight.

Suitable substrates are all materials of which capacitors, semiconductors, multilayer printed circuits or integrated circuits consist or from which they can be produced. In particular, surfaces comprising thermally oxidized and/or aluminum-coated silicon material, which may also be doped, including all other substrates conventionally used in semiconductor technology, such as, for example, silicon nitride, gallium arsenide and indium phosphide, may be mentioned. The substrates known from the production of liquid crystal displays, such as glass and indium tin oxide, as well as metal sheets and foils (for example of aluminum,trimetallic foils bimetallic and trimetallic foils and electrically nonconductive films which are coated with metals by vapor deposition and uncoated or aluminum-coated $SiO_2$ materials and paper, are also suitable. These substrates may be subjected to a heat pretreatment, may be roughened on the surface, etched or treated with chemicals to improve desired properties, for example the enhancement of the hydrophilic character.

In order to achieve better adhesion of the resist layer on the substrate, the mixture may contain an adhesion promoter. The substrate surface may also be pretreated with an adhesion promoter. In the case of silicon or silica substrates, adhesion promoters of the aminosilane type, such as 3-aminopropyltriethoxysilane or hexamethyldisilazane, are suitable for this purpose.

Suitable substrates for the production of printing plates (letterpress printing, lithographic printing, screen printing and relief copies) are aluminum sheets (if necessary anodically oxidized, grained and/or treated with silicate), zinc and steel sheets (if necessary chromium-plated) and plastic films or paper.

The recording material according to the invention is exposed imagewise. Sources of actinic light are: metal halide lamps, carbon arc lamps, xenon lamps and mercury vapor lamps. Exposure to high-density radiation, such as laser radiation, electron radiation or X-rays, is also possible. However, lamps which can emit light having a wavelength of 190 to 260 nm are particularly preferred, i.e. in particular xenon and/or mercury vapor lamps. Laser light sources, for example excimer lasers, in particular KrF or ArF lasers, which emit at 248 and 193 nm, respectively, may also be used. The radiation sources must have sufficient emission in the stated wavelength ranges.

The layer thickness varies depending on its field of use. It is from 0.1 to 100 µm, in particular from 1 to 10 µm.

The radiation-sensitive mixture can be applied to the substrate by spraying on, flow coating, roll coating, spin coating and immersion coating. Thereafter, the solvent is removed by evaporation so that the radiation-sensitive layer remains behind on the surface of the substrate. If required, removal of the solvent can be promoted by heating the layer to temperatures of up to 150° C. However, the mixture may also initially be applied in the abovementioned manner to a temporary substrate from which it is transferred under pressure and at elevated temperature to the final substrate. In principle, all materials also shown to be suitable substrates may be used as temporary substrates. The layer is then exposed imagewise. Thereafter, an image is revealed in the layer by treating the layer with a developer solution which dissolves or removes the exposed parts of the material.

In particular, aqueous solutions of silicates, metasilicates, hydroxides, hydrogen phosphates or dihydrogen phosphates, carbonates or bicarbonates are used as developers. Developers which are free of metal ions are preferred. The content of these substances in the developer solution is in general 0.1 to 15% by weight, preferably 0.5 to 5% by weight, based on the weight of the developer solution.

The developer may contain small amounts of a wetting agent in order to facilitate removal of the exposed parts in the developer.

The developed resist structures are, if required, postcured. This is generally effected by heating the resist structure on a hotplate to a temperature below the flow temperature and then exposing it uniformly to UV light from a xenon/mercury vapor lamp (range from 200 to 250 nm). As a result of this postcuring, the resist structures are crosslinked so that the structures have a flow resistance in general up to temperatures of above 200° C. The postcuring may also be effected without a temperature increase, by exposure to high-energy UV light.

The mixture according to the invention is preferably used in lithographic processes for the production of integrated circuits or of discrete electrical modules. The recording material produced from the mixture serves as a mask for the subsequent process steps. These include, for example, etching of the substrate, implantation of ions in the substrate or deposition of metals or other materials on the substrate.

PREPARATION EXAMPLE 1

A solution of 5 g (30 mmol) of 1-phenyl-2,2,2-trifluoroethanol in 100 ml of diethyl ether was added to a suspension of 1.05 g of sodium hydride (80% strength dispersion in mineral oil; 35 mmol) in 100 ml of diethyl ether. Stirring was carried out for 1 hour at room temperature, after which 5.7 g (30 mmol) of toluene-4-sulfonyl chloride, dissolved in 100 ml of diethyl ether, were added dropwise. The mixture was stirred for 8 hours at room temperature and allowed to stand overnight. After filtration of the salt, the organic phase was extracted by shaking with water and was dried. After evaporating down and recrystallizing the residue from petroleum ether/diethyl ether, 7.2 g of 2,2,2-trifluoro-1-phenyl-1-(toluene-4-sulfonyloxy)-ethane remained (colorless crystals, melting point (m.p.): 115° C.).

1-Phenyl-2,2,2-trifluoroethanol was obtained by reducing phenyl trifluoromethyl ketone with sodium borohydride.

PREPARATION EXAMPLE 2

0.9 g (30 mmol) of sodium hydride (80% strength dispersion in mineral oil) was added to 5 g (26 mmol) of 1,1,1-trifluoro-2-phenylpropan-2-ol in 125 ml of diethyl ether at room temperature. The mixture was stirred for about 1 hour, and 4.75 g (25 mmol) of toluene-4-sulfonyl chloride were then added in portions. Stirring was carried out for 60 hours at room temperature, after which the undissolved constituents were filtered off and the solution was then cooled. 4.3 g of 1,1,1-trifluoro-2-phenyl-2-(toluene-4-sulfonyloxy)-propane were obtained (colorless crystals, m.p.: 102° C. [recrystallized from diethyl ether]). After the mother liquor had been evaporated down, a further 1.6 g of the desired compound could be isolated.

1,1,1-Trifluoro-2-phenylpropan-2-ol was prepared from benzene and 1,1,1-trifluoroacetone by an $AlCl_3$-catalyzed Friedel-Crafts reaction.

PREPARATION EXAMPLE 3

5.2 g (25 mmol) of 1-cyano-2,2,2-trifluoro-1-phenylethanol were dissolved in 50 ml of DMF, and 0.9 g (30 mmol) of sodium hydride (80% strength dispersion in mineral oil) was added. 5.5 g (29 mmol) of toluene-4-sulfonyl chloride were added in portions to the virtually clear solution after about 1 hour. The mixture was stirred for 8 hours, allowed to stand overnight and then poured into water. The oily liquid which separated out solidified on cooling. The solid was filtered off with suction and dried. 6.3 g of 1-cyano-1-phenyl-1-(toluene-4-sulfonyloxy)-2,2,2-trifluoroethane were obtained (colorless crystals, m.p.: 70° C. [from ligroin]).

1-Cyano-1-phenyl-2,2,2-trifluoroethanol was prepared from α,α,α-trifluoroacetophenone by a cyanohydrin reaction with potassium cyanide.

PREPARATION EXAMPLE 4

5.16 g (20 mmol) of 1,1,1,3,3,3-hexafluoro-2-p-tolylpropan-2-ol were dissolved in 50 ml of methylene chloride, and 2.8 g (28 mmol) of triethylamine were added. 3.2 g (22 mmol) of methanesulfonyl chloride were added dropwise, while stirring, to the solution cooled to 5° C. After warming up to room temperature, the mixture was allowed to stand overnight. The precipitated salt was filtered off and the organic solution was evaporated down. The subsequent chromatography (silica gel/methylene chloride) gave 4.8 g of 2-methanesulfonyloxy-2-p-tolyl-1,1,1,3,3,3-hexafluoropropane (pale yellow oil).

1,1,1,3,3,3-Hexafluoro-p-tolylpropan-2-ol was prepared from toluene and hexafluoroacetone by an $AlCl_3$-catalyzed Friedel-Crafts reaction.

PREPARATION EXAMPLE 5

12 g (44.4 mmol) of 1,1,1,3,3,3-hexafluoro-2-(3-vinylphenyl)-propan-2-ol were dissolved in 50 ml of anhydrous DMF, and a spatula tip of 2-tert-butyl-hydroquinone (10 mg) was added for stabilization. 1.5 g (50 mmol) of sodium hydride were then added while stirring and cooling with ice at about 5° C. After everything had dissolved, 9.92 g (47mmol) of 4-chlorobenzenesulfonyl chloride were added at the same temperature. The mixture was stirred for 72 hours at room temperature, methylene chloride was then added and the mixture was washed with water, dried, filtered and evaporated down. The residue obtained was chromatographed with hexane/chloroform over a silica gel column. 16.65 g of 2-(4-chlorobenzenesulfonyloxy)-1,1,1,3,3,3-hexafluoro-2-(3-vinylphenyl)-propane (=2,2,2-trifluoro-1-trifluoromethyl-1-(3-vinylphenyl)-ethyl 4-chlorobenzenesulfonate) were isolated (colorless crystals, m.p.: 70° C.).

The 1,1,1,3,3,3-hexafluoro-2-(3-vinylphenyl)-propan-2-ol was obtained from 3-bromostyrene by reaction with (i) magnesium and (ii) hexafluoroacetone.

PREPARATION EXAMPLE 6

4.1 g (10 mmol) of 1,3-bis-(1-hydroxy-1-trifluoromethyl-2,2,2-trifluoroethyl)-benzene were dissolved in 50 ml of methylene chloride, and 2.5 g (25 mmol) of triethylamine were added. 3.64 g (25 mmol) of methanesulfonyl chloride were then added dropwise. The mixture was stirred for 8 hours at room temperature, separated off from the precipitated salt and evaporated down. 5.6 g of 1,3-bis-(1-methanesulfonyloxy-1-trifluoromethyl-2,2,2-trifluoroethyl)-benzene were obtained (colorless crystals, m.p.: 125° C. [from diisopropyl diether]).

PREPARATION EXAMPLE 7

10.1 g (15.2 mmol) of 1,1,1,3,3,3-hexafluoro-2,2-bis-[4-methyl-3-(2,2,2-trifluoro-1-hydroxy-1-trifluoromethylethyl)-phenyl]-propane were dissolved in 50 ml of methylene chloride, and 3.4 g (33 mmol) of triethylamine were added at 0° C. 4.0 g (34.7 mmol) of methanesulfonyl chloride in 20 ml of methylene chloride were added dropwise at 0° to 5° C. The mixture was stirred for 24 hours at room temperature, separated off from the precipitated salt, washed with water, dried and evaporated down. The oily residue was recrystallized. 9.2 g of 1,1,1,3,3,3-hexafluoro-2,2-bis-[4-methyl-3-(2,2,2-trifluoro-1-methanesulfonyloxy-1-trifluoromethyl-ethyl)-phenyl]-propane were obtained (colorless crystals, m.p.: 135° C. [from toluene]).

The starting compound was prepared from 1,1,1,3,3,3-hexafluoro-2,2-di-p-tolylpropane by reaction with (i) bromine, (ii) magnesium and (iii) hexafluoroacetone.

PREPARATION EXAMPLE 8

4.1 g (10 mmol) of 1,4-bis-(2,2,2-trifluoro-1-hydroxy-1-trifluoromethylethyl)-benzene were dissolved in 50 ml of methylene chloride, and 2.5 g (25 mmol) of triethylamine were added. 2.86 g (25 mmol) of methanesulfonyl chloride were added dropwise at 5° to 10° C. The mixture was stirred for 48 hours at room temperature, separated off from the precipitated salt, washed with water, dried and evaporated down. The residue was chromatographed over a silica gel column with methylene chloride/n-hexane (1:1). 3.2 g of 1,4-bis-(2,2,2-trifluoro-1-methanesulfonyloxy-1-trifluoromethylethyl)-benzene were obtained (colorless crystals, m.p.: 151° C. [from diisopropyl ether]).

1.4 g of 1-(2,2,2-trifluoro-1-methanesulfonyloxy-1-trifluoromethylethyl)-4-(2,2,2-trifluoro-1-hydroxy-1-trifluoromethylethyl)-benzene were isolated as a by-product (colorless crystals, m.p.: 160° C.).

PREPARATION EXAMPLE 9

4.25 g (10 mmol) of 2,4-bis-(2,2,2-trifluoro-1-hydroxy-1-trifluoromethylethyl)-toluene were dissolved in 50 ml of methylene chloride, and 2.5 g (25 mmol) of triethylamine were added. 2.86 g (25 mmol) of methanesulfonyl chloride were added dropwise at 5° to 10° C. The mixture was stirred for 16 hours at room temperature, separated off from the precipitated salt, washed with water, dried and evaporated down. The residue was chromatographed over a silica gel column with methylene chloride/n-hexane (1:1). After the eluate had been evaporated down, 2.9 g of 2,4-bis-(2,2,2-trifluoro-1-methanesulfonyloxy-1-trifluoromethylethyl)-toluene were obtained (colorless crystals, m.p.: 107° C.).

PREPARATION EXAMPLE 10

4.1 g (10 mmol) of 1,3-bis-(2,2,2-trifluoro-1-hydroxy-1-trifluoromethylethyl)-benzene were dissolved in 20 ml of dry DMF, and 0.75 g (25 mmol) of sodium hydride (80% strength dispersion) was added. The clear solution formed was stirred for a further 30 minutes. 3.22 g (25 mmol) of ethanesulfonyl chloride was then added dropwise at 10° to 15° C. The mixture was stirred for 48 hours at room temperature, separated off from the precipitated salt, washed with water, dried and evaporated down. The residue was eluted over a silica gel column with methylene chloride/n-hexane (1:1). 3.5 g of 1,3-bis-(1-ethanesulfonyloxy-2,2,2-trifluoro-1-trifluoro-methylethyl)-benzene were obtained (colorless crystals, m.p.: 67° C.).

1.2 g of 1-(1-ethanesulfonyloxy-2,2,2-trifluoro-1-trifluoromethylethyl)-3-(2,2,2-trifluoro-1-hydroxy-1-trifluoromethylethyl)-benzene were isolated as a by product (colorless crystals, m.p.: 64° C.).

PREPARATION EXAMPLE 11

4.27 g (10 mmol) of 2,4-bis-(2,2,2-trifluoro-1-hydroxy-1-trifluoromethylethyl)-phenol were dissolved in 40 ml of dry DMF, and 1.05 g (35 mmol) of sodium hydride (80% strength dispersion) were added. The clear solution formed was stirred for a further 30 minutes. 4.0 g (35 mmol) of methanesulfonyl chloride were added dropwise at 5° C. The mixture was stirred for 48 hours at room temperature and poured into ice water. The precipitate was separated off, washed with an aqueous ethanol solution and dried. The residue was chromatographed over a silica gel column with methylene chloride. 2.2 g of 1,3-bis-(2,2,2-trifluoro-1-methanesulfonyloxy-1-trifluoro-methylethyl)-4-methanesulfonyloxybenzene were obtained (colorless crystals, m.p.: 149° C.).

PREPARATION EXAMPLE 12

4.1 g (10 mmol) of 1,3-bis-(2,2,2-trifluoro-1-hydroxy-1-trifluoromethylethyl)-benzene were dissolved in 20 ml of dry DMF, and 0.75 g (25 mmol) of sodium hydride (80% strength dispersion) was added. The clear solution formed was stirred for a further 30 minutes. 4.75 g (25 mmol) of toluene-4-sulfonyl chloride in 15 ml of DMF were added dropwise at 10° to 15° C. The mixture was stirred for 48 hours at room temperature and poured into water. The crystalline precipitate was filtered off, washed with water and dried. The residue was chromatographed over a silica gel column with methylene chloride. 3.5 g of 1,3-bis-[2,2,2-trifluoro-1-(toluene-4-sulfonyloxy)-1-trifluoromethylethyl]-benzene were obtained (colorless crystals, m.p.: 131° C.).

PREPARATION EXAMPLE 13

4.1 g (10 mmol) of 1,3-bis-(2,2,2-trifluoro-1-hydroxy-1-trifluoromethylethyl)-benzene were dissolved in 20 ml of dry DMF, and 0.75 g (25 mmol) of sodium hydride (80% strength dispersion) was added. The clear solution formed was stirred for a further 30 minutes. 5.25 g (25 mmol) of 4-chlorobenzenesulfonyl chloride in 15 ml of DMF were then added dropwise at 10° to 15° C. The mixture was stirred for 48 hours at room temperature and poured into water. The crystalline precipitate was filtered off, rinsed with water and dried. The residue was chromatographed over a silica gel column with methylene chloride. 4.2 g of 1,3-bis-[1-(4-chlorobenzenesulfonyloxy)-2,2,2-trifluoro-1-trifluoromethylethyl]-benzene were obtained (colorless crystals, m.p.: 125° C.).

PREPARATION EXAMPLE 14

7.75 g (30 mmol) of 1,1,1,3,3,3-hexafluoro-2-p-tolylpropan-2-ol were dissolved in 45 ml of DMF, and 1.2 g (40 mmol) of NaH (80% strength dispersion in mineral oil) were added. After a clear solution had formed, 5.0 g (14 mmol) of 2,4,6-trimethylbenzene-1,3-disulfonyl chloride were added and the mixture was stirred for a further 72 hours at room temperature. The mixture was poured into water and the precipitated product was filtered off and dried. 7.8 g of 1,3,5-trimethyl-2,4-bis-(2,2,2-trifluoro-1-p-tolyl-1-trifluoromethylethoxy-sulfonyl)-benzene were obtained (colorless crystals, m.p.: 178° C. [from acetonitrile]).

PREPARATION EXAMPLE 14A 4.5 g (7.88 mmol) of 1,3,5-tris-(2,2,2-trifluoro-1-hydroxy-1-trifluoromethylethyl)-benzene were dissolved in 40 ml of dry DMF, and 0.95 g (31.5 mmol) of sodium hydride was added while flushing with nitrogen. After dissolution of the hydride, 6.56 g (30 mmol) of 4-isopropylbenzenesulfonyl chloride were added at 0 to 5° C. Slight evolution of heat was observed. The mixture was stirred for 20 hours at 5° C., ethyl acetate was added and the mixture was washed with water, dried, filtered and evaporated down. 9.6 g of crude product were obtained, and said crude product was eluted over a silica gel column with a 1:1 mixture of methylene chloride/hexane. The third fraction obtained was freed from the solvent and gave 6.8 g of 1,3,5-tris-[2,2,2-trifluoro-1-(4-isopropylbenzenesulfonyloxy)-1-trifluoromethylethyl]-benzene. M.p. 105° C.

PREPARATION EXAMPLES 15 to 209

The compounds of the general formula I which are shown below in Tables 1 and 1A and in which n=1 were prepared similarly to Preparation Examples 1 to 5, the number in the final column of the Table indicating the analogous Example in each case. Table 2 shows compounds of the general formula II in which fluorinated bis-(2-hydroxypropane) derivatives were esterified according to Preparation Examples 6 to 13 with two or three times the molar amount of sulfonyl chloride. Table 3 shows examples of compounds of the general formula I where n=2 or 3, in which a polyfunctional sulfonyl chloride was esterified according to Preparation Example 14 with fluorinated 2-hydroxypropane derivatives.

TABLE 1

Compounds of the general formula I
$R^1—C(CF_3)(R^2)—O—SO_2—R^3$

| No. | $R^1$ | $R^2$ | $R^3$ | according to Example |
|---|---|---|---|---|
| 15 | —C$_6$H$_5$ | —H | —C$_6$H$_4$—Cl(p) | 1 |
| 16 | —C$_6$H$_4$—CH$_3$(p) | —H | —C$_6$H$_4$—CH$_3$(p) | 1 |
| 17 | —C$_6$H$_4$—OCH$_3$(p) | —H | —C$_6$H$_4$—CH$_3$(p) | 1 |
| 18 | —C$_6$H$_4$Br(p)- | —H | —C$_6$H$_4$—CH$_3$(p) | 1 |
| 19 | —C$_6$H$_4$—CF$_3$(m) | —H | —C$_6$H$_4$—CH$_3$(p) | 1 |
| 20 | —C$_6$H$_5$ | —CH$_3$ | —C$_6$H$_4$—Cl(p) | 2 |
| 21 | —C$_6$H$_4$—CH$_3$(p) | —CH$_3$ | —C$_6$H$_4$—CH$_3$(p) | 2 |
| 22 | —C$_6$H$_4$—CH$_3$(m) | —CH$_3$ | —C$_6$H$_4$—CH$_3$(p) | 2 |
| 23 | —C$_6$H$_4$—C$_6$H$_5$(p) | —CH$_3$ | —C$_6$H$_4$—CH$_3$(P) | 2 |
| 24 | —C$_6$H$_4$Cl(p)- | —CH$_3$ | —C$_6$H$_4$—CH$_3$(p) | 2 |
| 25 | —C$_6$H$_4$Cl(m)- | —CH$_3$ | —C$_6$H$_4$—CH$_3$(p) | 2 |
| 26 | —C$_6$H$_4$—CF$_3$(p) | —CH$_3$ | —C$_6$H$_4$—CH$_3$(p) | 2 |
| 27 | —C$_6$H$_4$—CF$_3$(m) | —CH$_3$ | —C$_6$H$_4$—CH$_3$(p) | 2 |
| 28 | —C$_6$H$_5$ | —CN | —C$_6$H$_4$—CH$_3$(p) | 3 |
| 29 | —C$_6$H$_4$—CH$_3$(p) | —CN | —C$_6$H$_4$—CH$_3$(p) | 3 |

TABLE 1A

Compounds of the general formula I, in which $R^2 = -CF_3$

| No. | $R^1$ | $R^3$ | according to Example |
|---|---|---|---|
| 30 | $-C_6H_5$ | $-CH_3$ | 4 |
| 31 | $-C_6H_5$ | $-CF_3$ | * |
| 32 | $-C_6H_5$ | $-CH_2-C_2H_5$ | 5 |
| 33 | $-C_6H_5$ | $-CH_2-C_6H_5$ | 5 |
| 34 | $-C_6H_5$ | $-C_6H_4-CH_3(p)$ | 5 |
| 35 | $-C_6H_5$ | $-C_6H_4Cl(p)$ | 5 |
| 36 | $-C_6H_5$ | $-C_6H_4-NO_2(p)$ | 5 |
| 37 | $-C_6H_5$ | $-C_6H_4-CO_2CH_3(p)$ | 5 |
| 38 | $-C_6H_5$ | $-C_6H_4-CO_2CH_3(m)$ | 5 |
| 39 | $-C_6H_5$ | $-C_6H_4-OBu^n(p)$ | 5 |
| 40 | $-C_6H_5$ | $-C_6H_4-OCF_3(p)$ | 5 |
| 41 | $-C_6H_5$ | $-\beta-C_{10}H_7$ | 5 |
| 42 | $-C_6H_5$ | 5-Cl-thiophen-2-yl | 4 |
| 43 | $-C_6H_5$ | $4-C_6H_5-SO_2$-thiophen-2-yl | 5 |
| 44 | $-C_6H_4-CH_3(p)$ | $-C_2H_5$ | 4 |
| 45 | $-C_6H_4-CH_3(p)$ | $-C_4H_9$ | 5 |
| 46 | $-C_6H_4-CH_3(p)$ | $-C_{12}H_{25}$ | 5 |
| 47 | $-C_6H_4-CH_3(p)$ | $-C_6H_4-CH_3(p)$ | 5 |
| 48 | $-C_6H_4-CH_3(p)$ | $-C_6H_4Cl(p)-CH_3(o)$ | 5 |
| 49 | $-C_6H_4-CH_3(p)$ | $-C_6H_4Cl(p)$ | 5 |
| 50 | $-C_6H_4-CH_3(p)$ | $-C_6H_3F_2(2,4)-$ | 5 |
| 51 | $-C_6H_4-CH_3(p)$ | $-C_6H_3Cl_2(2,4)-$ | 5 |
| 52 | $-C_6H_4-CH_3(p)$ | $-C_6H_3Cl_2(3,4)-$ | 5 |
| 53 | $-C_6H_4-CH_3(p)$ | $-C_6H_3Cl_2(2,5)-$ | 5 |
| 54 | $-C_6H_4-CH_3(p)$ | $-C_6H_3Cl_2(3,5)$ | 5 |
| 55 | $-C_6H_4-CH_3(p)$ | $-C_6H_2Cl_3(2,3,4)$ | 5 |
| 56 | $-C_6H_4-CH_3(p)$ | $-C_6H_2Cl_3(2,4,6)$ | 5 |
| 57 | $-C_6H_4-CH_3(p)$ | $-C_6H_4-CN(o)$ | 5 |
| 58 | $-C_6H_4-CH_3(p)$ | $-C_6H_4-CH(CH_3)_2(p)$ | 5 |
| 59 | $-C_6H_4-CH_3(p)$ | $-C_6H_4-C(CH_3)_3(p)$ | 5 |
| 60 | $-C_6H_4-CH_3(p)$ | $-C_6H(CH_3)_4(2,3,5,6)$ | 5 |
| 61 | $-C_6H_4-CH_3(p)$ | $-C_6H_4-O-C_8H_{17}$ | 5 |
| 62 | $-C_6H_4-CH_3(p)$ | $-C_6H_4-O(CH_2)_2-C_6H_5$ | 5 |
| 63 | $-C_6H_4-CH_3(p)$ | $-C_6H_4-O(CH_2)_3-C_6H_5$ | 5 |
| 64 | $-C_6H_4-CH_3(p)$ | $-C_6H_4-O(CH_2)_2O-C_6H_5$ | 5 |
| 65 | $-C_6H_4-CH_3(p)$ | $-C_6H_4-O(CH_2)_3O-C_6H_5$ | 5 |
| 66 | $-C_6H_4-CH_3(p)$ | $-C_6(CH_3)_5$ | 5 |
| 67 | $-C_6H_4-CH_3(p)$ | $\beta-C_{10}H_7$ | 5 |
| 68 | $-C_6H_4-CH_3(p)$ | $4-Cl-\alpha-C_{10}H_6$ | 5 |
| 69 | $-C_6H_4-CH_3(p)$ | Anthraquinone-2-yl | 5 |
| 70 | $-C_6H_4-CH_3(p)$ | Thiophen-2-yl | 5 |
| 71 | $-C_6H_4-CH_3(p)$ | $2,5-Cl_2$-thiophen-3-yl | 5 |
| 72 | $-C_6H_4-CH_3(p)$ | $4,5-Br_2$-thiophen-2-yl | 5 |
| 73 | $-C_6H_4-CH(CH_3)_2(p)$ | $-C_6H_4F(m)$ | 5 |
| 74 | $-C_6H_4-Bu^n(p)$ | $-C_6H_2Cl_3(2,3,4)$ | 5 |
| 75 | $-C_6H_4-C(CH_3)_3(p)$ | $-CF_3$ | * |
| 76 | $-C_6H_3(CH_3)_2(2,5)$ | $-C_6H_4-C(CH_3)_2-C_2H_5(p)$ | 5 |
| 77 | $-C_6H_4F(p)$ | $-CH_3$ | 4 |
| 78 | $-C_6H_4F(p)$ | $-C_6H_4-CH_3(p)$ | 5 |
| 79 | $-C_6H_4F(p)$ | $-C_6H_4-O(CH_2)_2-C_6H_5$ | 5 |
| 80 | $-C_6H_4F(p)$ | $-C_6H_4-O(CH_2)_3-C_6H_5$ | 5 |
| 81 | $-C_6H_4F(p)$ | $-C_6H_4-O(CH_2)_3O-C_6H_5$ | 5 |
| 82 | $-C_6H_4Cl(p)$ | $-C_6H_4-CH_2-C_2H_5(p)$ | 5 |
| 83 | $-C_6H_4Cl(p)$ | $-C_6HF_2(3,6)Br_2(2,5)$ | 5 |
| 84 | $-C_6H_4Cl(p)$ | $-C_6H_4I(p)$ | 5 |
| 85 | $-C_6H_4Cl(p)$ | $-C_6H_4-O(CH_2)_3-C_6H_5(p)$ | 5 |
| 86 | $-C_6H_4Cl(m)$ | $-C_6H_4-CH_3(p)$ | 5 |
| 87 | $-C_6H_4Cl(o)$ | $-C_6H_4Br(p)$ | 5 |
| 88 | $-C_6H_4Br(p)$ | $-C_6H_4-CN(p)$ | 5 |
| 89 | $-C_6H_4OCH_3(o)$ | $-C_6H_4-O(CH_2)_2-C_6H_5(p)$ | 5 |
| 90 | $-C_6H_4-OCH_3(o)$ | $-C_6H_3Cl_2(2,3)$ | 5 |
| 91 | $-C_6H_4-OCH_3(o)$ | $\alpha-C_{10}H_7$ | 5 |
| 92 | $-C_6H_4-OCH_3(p)$ | $-C_2H_5$ | 4 |
| 93 | $-C_6H_4-OCH_3(p)$ | $-C_6H_4-CH_3(p)$ | 5 |
| 94 | $-C_6H_4-OCH_3(p)$ | $4,5-Br_2$-thiophen-2-yl | 5 |
| 95 | $-C_6H_3(OCH_3)_2(3,4)$ | $-C_6H_3Cl_2(3,4)$ | 5 |
| 96 | $-C_6H_4-OBu^n$ | $\beta-C_{10}H_7$ | 5 |
| 97 | $-C_6H_4-N(CH_3)_2(p)$ | $-C_6H_3F-CH_3(3,5)$ | 5 |
| 98 | $-C_6H_4-CH=CH_2(p)$ | $-CH_3$ | 4 |
| 99 | $-C_6H_4-CH=CH_2(p)$ | $-C_6H_4-CH_3(p)$ | 5 |
| 100 | $-C_6H_4-CH=CH_2(p)$ | $-C_6H_4-O(CH_2)_2-C_6H_5(p)$ | 5 |
| 101 | $-C_6H_4-CH=CH_2(p)$ | $-C_6H_4-O(CH_2)_3O-C_6H_5(p)$ | 5 |
| 102 | $-C_6H_4-CH=CH_2(p)$ | $-C_6H_4Cl(p)$ | 5 |
| 103 | $-C_6H_4-CH=CH_2(p)$ | $\beta-C_{10}H_7$ | 5 |

TABLE 1A-continued

Compounds of the general formula I, in which $R^2 = -CF_3$

| No. | $R^1$ | $R^3$ | according to Example |
|---|---|---|---|
| 104 | $-C_6H_4-CH=CH_2(m)$ | $-C_2H_5$ | 5 |
| 105 | $-C_6H_4-CH=CH_2(m)$ | $-C_6H_4-CH_3(p)$ | 5 |
| 106 | $-C_6H_4-CH=CH_2(m)$ | $-C_6H_4-OBu^n(p)$ | 5 |
| 107 | $-C_6H_4-CH=CH_2(m)$ | $-C_6H_4-OC_2H_4-C_6H_5(p)$ | 5 |
| 108 | $-C_6H_4-CH=CH_2(m)$ | $-C_6H_4-O(CH_2)_3O-C_6H_5(p)$ | 5 |
| 109 | $-C_6H_4-CH=CH-CH_3(m)$ | $-C_6H_4-CH_3(p)$ | 5 |
| 110 | $-C_6H_4-C\equiv C-CH_3(p)$ | $-C_2H_5$ | 5 |
| 111 | $-C_6H_4-C_6H_5(p)$ | $-CH_3$ | 4 |
| 112 | $-C_6H_4-C_6H_5(p)$ | $-C_2H_5$ | 5 |
| 113 | $-C_6H_4-C_6H_5(p)$ | $-C_6H_4-Cl(p)$ | 5 |
| 114 | $-C_6H_4-OCH_2-C_6H_5(p)$ | $-C_6H_4Br(p)$ | 5 |
| 115 | $-C_6H_4-OCH_2-C_6H_5(m)$ | $-C_6H_5$ | 5 |
| 116 | $-C_6H_4-SCH_3(p)$ | $-C_6H_3Cl_2(3,4)$ | 5 |
| 117 | $-C_6H_4-SO_2-CH_3(p)$ | $-C_2H_5$ | 4 |
| 118[a] | $-C_6H_4-O-SO_2-CH_3(p)$ | $-CH_3$ | 4 |
| 119[a] | $-C_6H_4-O-SO_2-C_2H_5(p)$ | $-C_2H_5$ | 4 |
| 120[a] | $-C_6H_4-NH-SO_2-CH_3(p)$ | $-CH_3$ | 4 |
| 121 | $-C_6H_4-C(CF_3)_2-OH(p)$ | $-CH_3$ | 5 |
| 122 | $-C_6H_4-C(CF_3)_2-OH(m)$ | $-CH_2-C_2H_5$ | 5 |
| 123 | $-C_6H_4-C(CF_3)_2-OH(m)$ | $-C_6H_4Cl(p)$ | 5 |
| 124 | $-C_6H_4-C(CF_3)_2-OH(m)$ | $-C_6H_3Cl_2(3,4)$ | 5 |
| 125 | $-C_6H_4-C(CF_3)_2OH(m)$ | $-C_6H_3-Cl_2(2,5)$ | 5 |
| 126 | $-C_6H_4-C(CF_3)_2OH(m)$ | $-C_6H_4-OCH_3(p)$ | 5 |
| 127 | $-C_6H_4-C(CF_3)_2-OH(m)$ | $-C_6H_3Br(3)-CH_3(4)$ | |
| 128 | $-C_6H_4-C(CF_3)_2-OH(m)$ | $-C_6H_4-NO_2(p)$ | |
| 128A | $-C_6H_3(-C(CF_3)_2-OCH_3)_2(3,5)$ | $-CH_3$ | |
| 128B | $-C_6H_3(-C(CF_3)_2-OCH_3)_2(3,5)$ | $-C_6H_4-CH_3(p)$ | |
| 128C | $-C_6H_3(-C(CF_3)_2-OCH_3)_2(3,5)$ | $-C_6H_4Cl(p)$ | |
| 128D | $-C_6H_3(-C(CF_3)_2-OCH_3)_2(3,5)$ | $-C_6H_4-NO_2(o)$ | |
| 128E | $-C_6H_3(-C(CF_3)_2-OCH_3)_2(3,5)$ | $\beta-C_{10}H_7$ | |
| 129[b] | $-C_6H_3(-O-SO_2-CH_3)_2(2,4)$ | $-C_6H_5$ | |
| 129A | $-C_6H_2(-O-SO_2-CH_3)_3(2,3,4)$ | $-CH_3$ | |
| 129B | $-C_6H_2(-O-SO_2-C_6H_4Cl(p))_3(2,3,4)$ | $-C_6H_4Cl(p)$ | |
| 130 | $\beta-C_{10}H_7$ | $-C_6H_4-CH_3(p)$ | |
| 131 | Thiophen-2-yl | $-C_6H_4-CH_3(p)$ | |
| 132 | Thiophen-2-yl | $-C_6H_4-NO_2(m)$ | |
| 133 | Benzo[b]thiophen-2-yl | $-C_6H_4-CH_3(p)$ | |
| 134 | Benzothiazol-5-yl | $-C_6H_4-CH_3(p)$ | |
| 135 | Quinolin-3-yl | $-C_6H_4-CH_3(p)$ | |

Compounds No. 127, 128, 129 and 130 to 135 are prepared according to Example 5
[a]Use twice the molar amount of sulfonyl chloride since an OH or NH group was reacted simultaneously in addition to the 2-hydroxypropane group
[b]Use three times the molar amount of sulfonyl chloride since two OH groups were reacted simultaneously in addition to the 2-hydroxypropane group.
*Preparation was carried out according to G. W. Astrologes et al., J. Amer. Chem. Soc. 99 (1977) 4400.
$Bu^n$ = n-Butyl (also in the following Tables)
$\alpha-C_{10}H_7$ = Naphth-1-yl
$\beta-C_{10}H_7$ = Naphth-2-yl Melting point of the compound:
128A=60° C.
128B=90° C.
128C=86° C.
128D=97° C.
128E=117° C.
129A=190° C.
129B=160° C.

TABLE 2

Compounds of the general formula
$R^1-[CR^2(CF_3)-O-SO_2-R^3]_2$,
where $R^2$ is $-CH_3$ in Examples 136 and 172 and $-CF_3$ in the other Examples

| No. | $R^1$ | $R^3$ |
|---|---|---|
| 136 | 1,3-$C_6H_4$ | $-CH_3$ |
| 137 | 1,3-$C_6H_4$ | $-C_2H_5$ |
| 138 | 1,3-$C_6H_4$ | $-CH_2-C_2H_5$ |
| 139 | 1,3-$C_6H_4$ | $-CH(CH_3)_2$ |
| 140 | 1,3-$C_6H_4$ | $-[CH_2]_3-CH_3$ |
| 141 | 1,3-$C_6H_4$ | $-C_2H_4-O-C_2H_5$ |
| 142 | 1,3-$C_6H_4$ | $-CH=CH_2$ |
| 143 | 1,4-$C_6H_4$ | $-C_2H_5$ |
| 144 | 1,4-$C_6H_4$ | $-CH_2-C_2H_5$ |
| 145 | 1,4-$C_6H_4$ | $-CH(CH_3)_2$ |
| 146 | 1,4-$C_6H_4$ | $-[CH_2]_3-CH_3$ |
| 147 | 1,3-$C_6H_4$ | $-C_6H_5$ |
| 148 | 1,3-$C_6H_4$ | $-C_6H_3(CH_3)_2(3,4)$ |
| 149 | 1,3-$C_6H_4$ | $-C_6H_4Br(p)$ |
| 150 | 1,3-$C_6H_4$ | $-C_6H_4Cl_2(2,4)$ |

TABLE 2-continued

Compounds of the general formula
$R^1$—[$CR^2(CF_3)$—O—$SO_2$—$R^3$]$_2$,
where $R^2$ is —$CH_3$ in Examples 136 and 172 and —$CF_3$ in the other Examples

| No. | $R^1$ | $R^3$ |
|---|---|---|
| 151 | 1,3-$C_6H_4$ | —$C_6H_4Cl_2$(3,4) |
| 152 | 1,3-$C_6H_4$ | —$C_6H_4$—OBu$^n$(p) |
| 153 | 1,3-$C_6H_4$ | —$C_6H_4$—$NO_2$(m) |
| 154 | 1,3-$C_6H_4$ | —$C_6H_4$—$NO_2$(p) |
| 155 | 1,3-$C_6H_4$ | —$CH_2$—$C_6H_5$ |
| 156 | 1,3-$C_6H_4$ | —CH=CH—$C_6H_5$ |
| 157 | 1,3-$C_6H_4$ | —$C_6H_4$—O($CH_2$)$_2$—$C_6H_5$(p) |
| 158 | 1,3-$C_6H_4$ | —$C_6H_4$—O($CH_2$)$_2$O—$C_6H_5$(p) |
| 159 | 1,3-$C_6H_4$ | —$C_6H_4$—O($CH_2$)$_3$O—$C_6H_5$(p) |
| 160 | 1,3-$C_6H_4$ | β—$C_{10}H_7$ |
| 161 | 1,3-$C_6H_4$ | 4-$C_6H_5$—$SO_2$-thiophen-2-yl |
| 162 | 1,4-$C_6H_4$ | —$C_6H_5$ |
| 163 | 1,4-$C_6H_4$ | —$C_6H_4$Cl(p) |
| 164 | 1,4-$C_6H_4$ | —$C_6H_4$—$CH_3$(p) |
| 165 | 1,4-$C_6H_4$ | —$CH_2$—$C_6H_5$ |
| 166 | 4-$CH_3$-1,3-$C_6H_3$ | —$CH_3$ |
| 167 | 4-$CH_3$-1,3-$C_6H_3$ | —$C_2H_5$ |
| 168 | 4-$CH_3$-1,3-$C_6H_3$ | —$C_6H_4$—$CH_3$(p) |
| 169 | 4-$CH_3$-1,3-$C_6H_3$ | —$C_6H_4$Cl(p) |
| 170 | 4-$CH_3$-1,3-$C_6H_3$ | —$C_6H_4$—O($CH_2$)$_2$O—$C_6H_5$(p) |
| 171* | 4-$CH_3SO_3$-1,3-$C_6H_4$ | —$C_6H_4$—$CH_3$(p) |
| 172 | 4,4'-$C_6H_4$—$C_6H_4$— | —$CH_3$ |
| 173 | 4,4'-$C_6H_4$—$C_6H_4$— | —$CH_3$ |
| 174 | 4,4'-$C_6H_4$—$C_6H_4$— | —$CH_2$—$C_2H_5$ |
| 175 | 4,4'-$C_6H_4$—$C_6H_4$— | —$C_6H_4$Cl(p) |
| 176 | 4,4'-$C_6H_4$—$C_6H_4$— | —$C_6H_4$—$OC_2H_5$ |
| 177 | 4,4'-$C_6H_4$—$C_6H_4$— | —β—$C_{10}H_7$ |
| 178 | 4,4'-$C_6H_4$—$C_6H_4$— | Benzo[b]thiophen-2-yl |
| 179 | 4,4'-$C_6H_4$—O—$C_6H_4$— | —$CH_3$ |
| 180 | 4,4'-$C_6H_4$—O—$C_6H_4$— | —$C_6H_4$—$CH_3$(p) |
| 181 | 3,3'-$C_6H_4$—C($CH_3$)$_2$—$C_6H_4$— | —$CH_3$ |
| 182 | 3,3'-$C_6H_4$—C($CH_3$)$_2$—$C_6H_4$— | —$C_6H_4$Cl(p) |
| 183 | 3,3'-$C_6H_4$—$SO_2$—$C_6H_4$— | —$CH_3$ |
| 184 | 3,3'-$C_6H_4$—$SO_2$—$C_6H_4$— | —$C_6H_4$—$CH_3$(p) |
| 185 | 3,3'-$C_6H_4$—CO—$C_6H_4$— | —$CH_3$ |
| 186 | 3,3'-$C_6H_4$—CO—$C_6H_4$— | —$C_6H_4$—$CH_3$(p) |
| 187 | 3,3'-$C_6H_4$—C($CF_3$)$_2$—$C_6H_4$— | —$CH_3$ |
| 188 | 3,3'-$C_6H_4$—C($CF_3$)$_2$—$C_6H_4$— | —$C_6H_4$—$CH_3$(p) |
| 189 | 3,3'-$C_6H_4$—C($CF_3$)$_2$—$C_6H_4$— | —$C_6H_4$—O($CH_2$)$_2$—$OC_6H_5$(p) |

*Prepared using three times the molar amount of sulfonyl chloride since a phenolic hydroxy group had to be esterified in addition to the two aliphatic hydroxyl groups.

TABLE 3

Compounds of the general formula $R^3$—[$SO_2$—O—C($CF_3$)($R^2$)—$R^1$]$_n$ in which $R^2$ is —$CF_3$

| No. | $R^1$ | n | $R^3$ |
|---|---|---|---|
| 190 | —$C_6H_5$ | 2 | —$CH_2$— |
| 191 | —$C_6H_4$—$CH_3$(p) | 2 | —$CH_2$— |
| 192 | —$C_6H_4$—$OCH_3$(o) | 2 | —$CH_2$— |
| 193 | —$C_6H_4$F(p) | 2 | —$C_3H_6$— |
| 194 | —$C_6H_4$F(p) | 2 | —$C_4H_8$— |
| 195 | —$C_6H_5$ | 2 | 1,3-$C_6H_4$— |
| 196 | —$C_6H_4$—$CH_3$(p) | 2 | 1,3-$C_6H_4$— |
| 197 | —$C_6H_4$—CH($CH_3$)$_2$(p) | 2 | 1,3-$C_6H_4$— |
| 198 | —$C_6H_3$($CH_3$)$_2$(2,4) | 2 | 1,3-$C_6H_4$— |
| 199 | —$C_6H_4$F(p) | 2 | 1,3-$C_6H_4$— |
| 200 | —$C_6H_4$Cl(p) | 2 | 1,3-$C_6H_4$— |
| 201 | —$C_6H_4$—$C_6H_5$(p) | 2 | 1,3-$C_6H_4$— |
| 202 | —$C_6H_5$ | 2 | 2,4,6-($CH_3$)$_3$-1,3-$C_6$H— |
| 203 | —$C_6H_4$Cl(m) | 2 | 2,4,6-($CH_3$)$_3$-1,3-$C_6$H— |
| 204 | —$C_6H_5$ | 2 | 1,5-$C_{10}H_6$— |
| 205 | —$C_6H_4$—$CH_3$(p) | 2 | 1,5-$C_{10}H_6$— |
| 206 | —$C_6H_5$ | 2 | 2,6-$C_{10}H_6$— |
| 207 | —$C_6H_4$—$CH_3$(p) | 2 | 2,6-$C_{10}H_6$— |
| 207A | —$CH_3$ | 3 | 1,3,5-$C_6H_3$*** |
| 207B | —$CH_2$—$C_2H_5$ | 3 | 1,3,5-$C_6H_3$*** |

TABLE 3-continued

Compounds of the general formula $R^3$—[$SO_2$—O—C($CF_3$)($R^2$)—$R^1$]$_n$ in which $R^2$ is —$CF_3$

| No. | $R^1$ | n | $R^3$ |
|---|---|---|---|
| 207C | —$C_6H_4$Cl(p) | 3 | 1,3,5-$C_6H_3$*** |
| 207D | β—$C_{10}H_7$ | 3 | 1,3,5-$C_6H_3$*** |
| 208 | —$C_6H_5$ | 3 | 1,3,7-$C_{10}H_5$—** |
| 209 | —$C_6H_4$—$CH_3$(p) | 3 | 1,3,7-$C_{10}H_5$—** |

*1,5-$C_{10}H_6$ = Naphthalene-1,5-diyl
**1,3,7-$C_{10}H_5$ = Naphthalene-1,3,7-triyl
***Benzene-1,3,5-triyl The Examples described below are merely a selection from the inventive concept. The latter is therefore not intended to be restricted to the Examples.

EXAMPLE 1

A coating solution was prepared from 6.86 parts by weight of a poly(4-hydroxystyrene) having an average molecular weight ($M_w$) of 18,800 g/mol, 2.94 parts by weight of a poly-N,O-acetal obtained from benzaldehyde and 2-hydroxyethyl n-propylcarbamate ($M_w$=8,700 g/mol), 0.2 part by weight of 2,2,2-trifluoro-1-trifluoro-methyl-1-(3-vinylphenyl)-ethyl 4-chlorobenzenesulfonate (cf. Preparation Example 5) and 40 parts by weight of propylene glycol monomethyl ether acetate.

The solution was filtered through a filter having a pore diameter of 0.2 μm and applied to a silicon wafer treated with an adhesion promoter (hexamethyldisilazane), by spin-coating, so that a layer thickness of 1.04 μm was obtained after drying at 120° C. for 1 minute on a hotplate.

The positive-working recording material was exposed imagewise under an original to the UV radiation from a xenon/mercury vapor lamp at 254 nm having an energy of 8 mJ/cm$^2$. 4 minutes after exposure, the mixture was further heated to 60° C. for 60 seconds on a hotplate.

The recording material was then developed with a 0.21N aqueous solution of tetramethylammoniumhydroxide (TMAH). After a development time of 60 seconds at 21° C., the irradiated parts had been completely removed. The mask had been exactly reproduced. Even the small structures of the mask having a size of 350 nm or less were reproduced true to detail.

EXAMPLE 2

A coating solution was prepared from 7.0 parts by weight of a copolymer of 2 parts of 3-methyl-4-hydroxystyrene and 1 part of 4-hydroxystyrene ($M_w$= 14,000 g/mol), having an OH number of 425 mg/g, 3.0 parts by weight of a poly-N,O-acetal obtained from 1 part of benzaldehyde and 1 part of 2-hydroxyethyl polycarbamate ($M_w$=5,000), 0.25 part by weight of 2,2,2-trifluoro-1-p-tolyl-1-trifluoromethylethyl 4-chlorobenzenesulfonate (compound No. 49 in Table 1) and 40 parts by weight of propylene glycol monomethyl ether acetate.

The solution was pretreated as described in Example 1 and applied to the wafer. After drying, a layer having a thickness of 1.02 μm remained.

The recording material was exposed imagewise under an original to the UV radiation from a xenon/mercury vapor lamp at 254 nm having an energy of 20 mJ/cm$^2$. After 4 minutes, the mixture was further heated to 60° C. for 60 seconds on a hotplate.

The recording material was then developed with a 0.27N aqueous TMAH solution. Once again, the mask was exactly reproduced down to structures having a size of 300 nm.

EXAMPLE 3

A wafer coated as in Example 1 was exposed under an original to the UV radiation from a KrF excimer laser (248 nm) having an energy of 9 mJ/cm$^2$. The material was stored for 4 minutes and then further heated and developed as described above. The resolution of the recording material proved to be excellent. The wall slope in the case of 350 nm structures was better than 87°.

EXAMPLE 4

A wafer coated as in Example 1 was exposed under an original to the UV radiation from a KrF excimer laser (248 nm) having an energy of 9 mJ/cm$^2$ (same dose as in Example 3) and was stored for 60 minutes at room temperature before further heating. During the development, an image which corresponded to that of Example 3 was obtained. Thus, the storage time between exposure and further heating was not found to have any effect on the exposure dose.

EXAMPLE 5

A coating solution was prepared from 7.5 parts by weight of a copolymer of styrene and 4-hydroxystyrene (20/80) ($M_w$=28,000), 3.1 parts by weight of piperonal bis(phenoxyethyl)-acetal, 0.45 part by weight of 2,2,2-trifluoro-1-p-tolyl-1-trifluoromethylethyl 4-(2-phenoxy-ethoxy)-benzenesulfonate (compound No. 64) and 30 parts by weight of propylene glycol monomethyl ether acetate.

The solution was pretreated and coated as described in Example 2. The 1.2 μm thick film was exposed imagewise under an original to the UV radiation from a xenon/mercury vapor lamp at 254 nm having an energy of 28 mJ/cm$^2$. After 5 minutes, the mixture was further heated to 70° C. for 60 seconds on a hotplate.

The recording material was then developed with 0.18N aqueous TMAH solution. Structures smaller than 500 nm in size were reproduced true to detail. The contrast of the material was >4.

EXAMPLE 6

A coating solution was prepared from 7.0 parts by weight of a homopolymer of 3-methyl-4-hydroxystyrene having an average molecular weight of 17,000 and an OH number of 385 mg/g, 3.0 parts by weight of a poly-N,O-acetal obtained from 1 part of benzaldehyde and 1 part of 2-hydroxyethyl propylcarbamate ($M_w$=3,500), 0.2 part by weight of 2,2,2-trifluoro-1-trifluoro-methyl-1-(4-vinylphenyl)-ethyl naphthalene-2-sulfonate (compound No. 103 in Table 1) and 40 parts by weight of propylene glycol monomethyl ether acetate.

After a standard pretreatment, the resulting 1.02 μm thick film was exposed under an original to KrF excimer laser radiation in a dose of 18 mJ/cm$^2$. After 5 minutes, the mixture was further heated to 60° C. for 60 seconds on a hotplate.

The recording material was then developed with 0.27N aqueous TMAH solution. The mask was exactly reproduced as described in the above Example. Even structures of <400 nm were reproduced true to detail.

EXAMPLE 7

The coating solution from Example 6 was changed in such a way that, instead of the poly-N,O-acetal, a polyorthoester prepared by condensation of trimethyl orthoformate and 7,7-bis-hydroxymethylnonan-1-ol was used.

After the usual pretreatment, the mixture was dried at 110° C. to give a film thickness of 1.06 μm.

The recording material was exposed imagewise under an original to UV radiation from a xenon/mercury vapor lamp at 254 nm having an energy of 11 mJ/cm$^2$. After 5 minutes, the wafer was further heated to 65° C. for 60 seconds on a hotplate.

Development was then effected with a 0.24N aqueous TMAH solution. The material resolved the original details of the mask down to structures of 600 nm.

EXAMPLE 8

A coating solution was prepared from 6.5 parts by weight of a copolymer of 1.5 parts of 3-methyl-4-hydroxystyrene and 1 part of 4-hydroxystyrene, having an average molecular weight of 14,000 and an OH number of 410 mg/g, 3.5 parts by weight of a poly-N,O-acetal obtained from 1 part of benzaldehyde and 1 part of 2-hydroxyethyl propylcarbamate, 0.3 part by weight of 2,2,2-trifluoro-1-phenyl-1-trifluoromethylethyl propanesulfonate (compound No. 32 in Table 1A) and 40 parts by weight of propylene glycol monomethyl ether acetate.

The solution was filtered through a filter having a pore diameter of 0.2 μm and applied, by spin-coating at 3000 revolutions, to two silicon wafers treated with an adhesion promoter (hexamethyldisilazane). After drying at 120° C. for 1 minute on a hotplate, a layer thickness of 0.99±0.03 μm was obtained.

The recording material was exposed imagewise under an original to UV radiation from a xenon/mercury vapor lamp at 254 nm having an energy of 16 mJ/cm$^2$. After 5 minutes in the case of one wafer and after 60 minutes in the case of the second wafer, heating to 60° C. was carried out for 60 seconds on a hotplate.

The exposed wafers were then developed with a 0.24N aqueous TMAH solution. The mask was exactly reproduced, similarly to that described in the Example above. In both cases, 350 nm structures were clearly resolved. The change in the line width was only slight.

EXAMPLE 9

A coating solution was prepared from 6.5 parts by weight of a copolymer of 2 parts of 3-methyl-4-hydroxystyrene and 1 part of 4-hydroxystyrene, having an average molecular weight of 14,000, 3.5 parts by weight of a poly-N,O-acetal obtained from 1 part of benzaldehyde and 1 part of 2-hydroxyethyl propylcarbamate, 0.4 part by weight of 2,2,2-trifluoro-1-trifluoro-methyl-1-(3-vinylphenyl)-ethyl 4-butoxybenzenesulfonate (compound No. 106 in Table 1A) and 40 parts by weight of propylene glycol monomethyl ether acetate.

The solution was filtered through a filter having a pore diameter of 0.2 µm and applied, by spin-coating at 3000 revolutions, to three silicon wafers treated with an adhesion promoter (hexamethyldisilazane). After drying at 120° C. for 1 minute on a hotplate, a layer thickness of 1.02±0.03 µm was obtained.

The recording material was exposed imagewise under an original to UV radiation from a KrF excimer laser having an energy range of from 15 to 22 mJ/cm². After 5 minutes in the case of the first wafer, after 60 minutes in the case of the second wafer and after 120 minutes in the case of the third wafer, heating to 60° C. was carried out for 60 seconds on a hotplate.

The exposed wafers were then developed with a 0.27N aqueous TMAH solution. In all three cases, the best results were obtained at a constant exposure dose of 18 mJ/cm²: the flanks were vertical and the resolution limit was 0.25 µm. In the case of the wafer stored for 120 minutes, a slightly more pronounced undercutting of the structures was detectable.

EXAMPLE 10

0.3 part by weight of an amine ((®)Tinuvin 440) was added to the coating solution of Example 9. The procedure was continued as described in Example 9, an exposure dose of 24 mJ/cm² being required for dimensionally accurate reproduction of the mask. Once again, all wafers could be developed in the same quality at this dose. Undercutting was not observed, even after 120 minutes.

EXAMPLE 11

The recording material of Example 9 was exposed imagewise to electron radiation having an energy of 8.32 µC/cm² (20 keV). The script was clearly recognizable after the processing described in Example 9.

EXAMPLE 12

A coating solution was prepared from 9.6 parts by weight of a copolymer of pyrocatechol monomethacrylate and tert-butoxycarbonyl pyrocatechol monomethacrylate (25:75), 0.5 part by weight of 2,2,2-trifluoro-1-p-tolyl-1-trifluoromethylethyl 3,5-dichlorobenzenesulfonate (compound No. 54) and 40 parts by weight of propylene glycol monomethyl ether acetate.

After a pretreatment was carried out similarly to Example 1, a film having a thickness of 0.8 µm was obtained by drying at 110° C. for 1 minute.

The recording material was exposed to a dose of 11 mJ/cm² according to Example 2, further heated to 100° C. for 1 minute and immersed for 1 minute in a 0.3N aqueous TMAH developer. Exact reproduction of the original was obtained, even structures smaller than 0.5 µm being satisfactorily resolved.

EXAMPLE 13

A coating solution was prepared from 6.86 parts by weight of a poly(4-hydroxystyrene) having an average molecular weight ($M_w$) of 18,800 g/mol, 2.94 parts by weight of a poly-N,O-acetal obtained from benzaldehyde and 2-hydroxyethyl n-propylcarbamate ($M_2$=8,700 g/mol), 0.2 part by weight of 1,3-bis-(2,2,2-trifluoro-1-methanesulfonyloxy-1-trifluoromethylethyl)-benzene (compound of Preparation Example No. 6) and 40 parts by weight of propylene glycol monomethyl ether acetate.

The solution was filtered through a filter having a pore diameter of 0.2 µm and applied by spin coating to a silicon wafer treated with an adhesion promoter (hexamethyldisilazane), so that, after drying at 120° C. for 1 minute on a hotplate, a layer thickness of 1.06 µm was obtained.

The positive-working recording material was exposed imagewise under an original to UV radiation from a xenon/mercury vapor lamp at 254 nm having an energy of 8.6 mJ/cm². 4 minutes after the exposure, the mixture was further heated to 60° C. for 60 seconds on a hotplate.

The recording material was then developed with a 0.21N aqueous TMAH solution. After 60 seconds at 21° C., the irradiated parts had been completely removed. The mask was exactly reproduced in the positive image obtained. Even the small structures of the mask having a size of 350 nm or less were reproduced true to detail.

EXAMPLE 14

A coating solution was prepared from 8.0 parts by weight of a copolymer of 3-methyl-4-hydroxystyrene/4-hydroxystyrene (molar ratio 75:25), having a mean softening point of >150° C. and an average molecular weight of 28,000, 2.0 parts by weight of hexa-N-methoxymethylmelamine and 0.5 part by weight of 1,4-bis-(2,2,2-trifluoro-1-methanesulfonyloxy-1-trifluoromethylethyl)-benzene (compound of Preparation Example No. 8) in 42 parts by weight of propylene glycol monomethyl ether acetate.

The mixture was pretreated as described in Example 1, applied to a wafer and dried at 110° C. for 1 minute to give a film thickness of 1.01 µm.

Exposure was effected through a negative original to radiation from a xenon/mercury vapor lamp (254 nm) in a dose of 4.2 mJ/cm². The mixture was then heated to 120° C. for 2 minutes on a hotplate.

The mixture was immersed for 1 minute in a 0.27N aqueous TMAH developer, even very fine unexposed details of the original being removed. The negative image obtained had a resolution down to structures of 0.35 µm.

EXAMPLE 15

A coating solution was prepared from 7.0 parts by weight of the copolymer described in Example 1, 3.0 parts by weight of the poly-N,O-acetal described in Example 1, 0.4 part by weight of 1,3-bis-(2,2,2-trifluoro-1-methanesulfonyloxy-1-trifluoromethylethyl)-benzene according to Preparation Example 6 as a photosensitive acid generator producing methanesulfonic acid and 40 parts by weight of propylene glycol monomethyl ether acetate.

COMPARATIVE EXAMPLES 16 to 21

Coating solutions were prepared according to Example 15, the photosensitive acid generator being replaced in said solutions as follows:

16: 2,6-Dinitrobenzyl methanesulfonate
17: Benzoin methanesulfonate
18: Pyrogallol trismethanesulfonate
19: N-Methanesulfonyloxysuccinimide
20: 1-Methanesulfonyloxy-4-methyl-6-phenylpyrid-2-one
21: 2-Methanesulfonyloxy-2-p-tolylpropane The solutions according to Example 15 and Comparative Examples 16 to 21 were filtered and were each applied by spin-coating to two wafers. After drying at 110° C., the layer thickness in all cases was 1.0±0.04 µm.

The transmittance of the films for radiation having a wavelength of 248 nm increased in the sequence 17<16<20<21<15=18=19, i.e. only the films of Comparative Examples 18 and 19 had an advantageous transparency similar to that of Example 15.

The recording materials were exposed imagewise under an original to UV radiation from a xenon/mercury vapor lamp at 254 nm. The exposure dose required for reproduction was from 5.5 mJ/cm² to 75 mJ/cm² (5.5 mJ/cm²=15=19<18<20<16<17<<21=75 mJ/cm²). After 5 minutes for one of the wafers in each case and after 60 minutes for the second wafer, further heating to 60° C. was carried out for 60 seconds on a hotplate.

The exposed wafers were then developed with a 0.27N aqueous TMAH solution. In the case of the materials stored for 5 minutes, the mask was reproduced down to 400 nm by all materials. Structures of <400 nm were resolved by the recording materials of Examples 15, 18, 19 and 21. in the case of the wafers exposed to the same dose and stored for 60 minutes, reproductions in the region of 450 nm could be obtained only with the recording materials of Examples 15 and 18; in all others, the structures of this size had been completely eliminated. Structures in the region of 350 nm or less were reproduced only by the recording material of Example 15, but with a clearly detectable undercut. These results show that the latent image of the recording materials is considerably stabilized when the mixture according to the invention is used and a constancy of exposure dose independent of the storage time is ensured only with these materials. The result obtained with the mixtures according to the invention can be further improved if basic additives, for example amines, are added to the mixture (cf. Example 10).

EXAMPLE 22

A coating solution was prepared from 8.0 parts by weight of a copolymer of 3-methyl-4-hydroxystyrene/4-hydroxystyrene (molar ratio 75:25), having a mean softening point >150° C. and an average molecular weight of 28,000, 2.0 parts by weight of hexa-N-methoxymethylmelamine and 0.5 part by weight of 2,2,2-trifluoro-1-phenyl-1-trifluoromethylethyl 5-chlorothiophene-2-sulfonate (compound No. 42) in 42 parts by weight of propylene glycol monomethyl ether acetate.

The mixture was pretreated as described in Example 1, applied to a wafer and dried at 110° C. for 1 minute to give a film thickness of 1.03 µm.

Exposure was effected through a negative original to radiation from a xenon/mercury vapor lamp (254 nm) in a dose of 3.8 mJ/cm². The mixture was then heated to 120° C. for 2 minutes on a hotplate.

The mixture was immersed for 1 minute in a 0.27N aqueous TMAH developer, even very fine unexposed details of the original being removed. The negative image obtained had a resolution down to structures of 0.35 µm.

EXAMPLE 23

A coating solution was prepared from 7.5 parts by weight of a homopolymer of 3-methyl-4-hydroxystyrene, having an average molecular weight of 14,000, 2.5 parts by weight of 4,4'-bismethoxymethyldiphenyl ether and 0.5 part by weight of 1-(4-chlorophenyl)-2,2,2-tri-fluoro-1-trifluoromethylethyl 4-(3-phenylpropoxy)-benzenesulfonate (compound No. 85) in 42 parts by weight of propylene glycol monomethyl ether.

The mixture was pretreated as described in Example 1, applied to a wafer and dried at 110° C. for 1 minute to give a film thickness of 0.98 µm.

Exposure was effected through a negative original to radiation from a xenon/mercury vapor lamp (254 nm) in a dose of 7.6 mJ/cm². The mixture was then heated to 115° C. for 2 minutes on a hotplate.

The mixture was immersed for 1 minute in a 0.27N aqueous TMAH developer, even very fine unexposed details of the original being removed. The negative image obtained had a resolution down to structures of 0.45 µm.

EXAMPLES 24 to 72

Coating solutions were prepared analogously to Example 1 (tonality +) or Example 22 (tonality −), the sulfonic acid esters stated in the Table below being used in the same amount by weight. Processing was effected as stated in the Examples. The sensitivity and resolution of small lines (not optimized) are stated below. The Examples are intended to show that highly sensitive recording materials can be produced virtually with all compounds according to the invention, of the formulae I and/or II, and their sensitivity is determined mainly by the presence of the —C(CF$_3$)R—O—SO$_2$ group.

| No. | Compound No. | Tonality | Sensitivity (mJ/cm²) | Resolution (µm) |
| --- | --- | --- | --- | --- |
| 24 | 18 | + | 32 | <0.4 |
| 25 | 23 | + | 22 | 0.4 |
| 26 | 28 | + | 25 | <0.4 |
| 27 | 34 | − | 16 | <0.4 |
| 28 | 39 | + | 22 | <0.4 |
| 29 | 40 | + | 16 | <0.4 |
| 30 | 45 | + | 28 | <0.4 |
| 31 | 46 | + | 35 | 0.4 |
| 32 | 49 | + | 17 | <0.4 |
| 33 | 52 | + | 14 | <0.4 |
| 34 | 55 | + | 12 | <0.4 |
| 35 | 61 | + | 45 | 0.4 |
| 36 | 64 | + | 38 | <0.4 |
| 37 | 68 | + | 32 | <0.4 |
| 38 | 79 | + | 29 | <0.4 |
| 39 | 83 | − | 14 | <0.4 |
| 40 | 94 | − | 21 | 0.4 |
| 41 | 98 | + | 8,2 | <0.4 |
| 42 | 101 | + | 11 | <0.4 |
| 43 | 103 | + | 12 | <0.4 |
| 44 | 104 | + | 7,5 | <0.4 |
| 45 | 108 | + | 10 | <0.4 |
| 46 | 111 | + | 7 | <0.4 |
| 47 | 114 | + | 9,5 | <0.4 |
| 48 | 125 | + | 8,2 | <0.4 |
| 49 | 130 | + | 18 | 0.4 |
| 50 | 134 | + | 22 | 0.4 |

-continued

| No. | Compound No. | Tonality | Sensitivity (mJ/cm$^2$) | Resolution (μm) |
|---|---|---|---|---|
| 51 | 138 | + | 11 | <0.4 |
| 52 | 142 | + | 10 | <0.4 |
| 53 | 149 | + | 6 | <0.4 |
| 54 | 151 | + | <6 | <0.4 |
| 55 | 156 | + | 8 | <0.4 |
| 56 | 158 | + | 11 | <0.4 |
| 57 | 158 | − | 9 | <0.4 |
| 58 | 160 | + | 12 | <0.4 |
| 59 | 166 | + | 8 | <0.4 |
| 60 | 169 | + | 4,5 | <0.4 |
| 61 | 173 | + | 11 | <0.4 |
| 62 | 179 | + | 9 | <0.4 |
| 63 | 183 | + | 7 | <0.4 |
| 64 | 183 | − | 6 | <0.4 |
| 65 | 187 | + | 7 | <0.4 |
| 66 | 187 | − | 6 | <0.4 |
| 67 | 189 | + | 12 | <0.4 |
| 68 | 193 | + | 22 | 0.4 |
| 69 | 196 | + | 19 | <0.4 |
| 70 | 196 | − | 13 | <0.4 |
| 71 | 202 | + | 19 | <0.4 |
| 72 | 207 | + | 17 | 0.4 |

We claim:

1. Radiation-sensitive, positive-working or negative-working mixture comprising
   a) a compound forming a strong acid on irradiation,
   b) either, for a positive-working mixture, a compound having at least one acid-cleavable C—O—C or C—O—Si bond or, for a negative-working mixture, a compound having at least two acid-crosslinkable groups and
   c) a binder which is insoluble in water but soluble or at least swellable in aqueous alkaline solutions,
wherein the compound a) is a sulfonic acid ester of the formula

   (I)

or

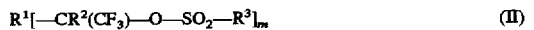   (II)

in which $R^1$ in the compounds of the formula I is a mononuclear or polynuclear unfused or fused ($C_6$–$C_{14}$)aryl- or ($C_4$–$C_{11}$)heteroaryl radical containing oxygen, sulfur or nitrogen as a heteroatom and, in the compounds of the formula II, a divalent or trivalent radical of a mononuclear or polynuclear unfused or fused ($C_6$–$C_{14}$) aromatic or ($C_4$–$C_{12}$)heteroaromatic containing oxygen, sulfur or nitrogen as a heteroatom or a divalent radical of the formula —$C_6H_4$—X—$C_6H_4$—, in which X is an oxygen atom, a carbonyl or sulfonyl group or a group $CR^7R^8$, in which $R^7$ and $R^8$ are identical or different and are a methyl or trifluoromethyl radical, $R^2$ is a hydrogen atom or a methyl, trifluoromethyl or cyano radical, $R^3$ in the compounds of the formula I where n=1 and in the compounds of the formula II is a straight-chain or branched, unsubstituted or substituted ($C_1$–$C_{18}$)alkyl radical, a ($C_4$–$C_{10}$)-cycloalkyl radical, a ($C_2$–$C_6$) alkenyl radical, an unsubstituted or substituted ($C_6$–$C_{14}$)aryl or ($C_4$–$C_{12}$)heteroaryl radical containing oxygen, sulfur or nitrogen as a heteroatom or a ($C_7$–$C_{18}$)aralkyl radical and, in the compounds of the formula I where n=2 or 3, a divalent or trivalent radical of a straight-chain or branched, unsubstituted or substituted ($C_1$–$C_{18}$)alkane or cycloalkane, of a mononuclear or polynuclear ($C_6$–$C_{14}$)aromatic or of a ($C_4$–$C_{12}$)heteroaromatic containing oxygen, sulfur or nitrogen as a heteroatom, and n is an integer from 1 to 3 and m is 2 or 3.

2. The radiation-sensitive mixture as claimed in claim 1, wherein $R^1$ in compounds of formula I is a phenyl, naphthyl, thiophen-2-yl, thiophen-3-yl, benzothiophen-2-yl, benzothiophen-3-yl or a phenyl radical to which a five-membered or six-membered ring having 1 to 3 heteroatoms is fused.

3. The radiation-sensitive mixture as claimed in claim 2, wherein the radical $R^1$ in compounds of formula I is substituted by one to three identical or different substituents, selected from the group consisting of fluorine, chlorine, bromine, ($C_1$–$C_6$)alkyl, ($C_2$–$C_6$)alkenyl, ($C_2$–$C_4$)alkynyl, ($C_1$–$C_6$)alkoxy, ($C_6$–$C_{10}$)aryl,($C_6$–$C_{10}$)aryloxy, ($C_7$–$C_{14}$) aralkyl, ($C_7$–$C_{14}$)aryloxyalky, ($C_7$–$C_{14}$)aryloxyalkoxy, ($C_1$–$C_6$)alkylthio, ($C_6$–$C_{10}$)arylthio, ($C_1$–$C_4$)dialkylamino, ($C_1$–$C_6$)carboxyalkyl, cyano, nitro, ($C_1$–$C_{10}$)alkanesulfonyl, ($C_6$–$C_{14}$)arylsulfonyl groups, $R^3$—$SO_2$—O—, $R^3$—$SO_2$—NH—, HO—C($CF_3$)—$R^2$— and $R^3$—$SO_2$—O—C($CF_3$) $R^2$—, in which $R^2$ is a hydrogen atom or a methyl, trifluoromethyl or cyano radical, $R^3$ in the compounds of the formula I where n=1 and in the compounds of the formula II is a straight-chain or branched, unsubstituted or substituted ($C_1$–$C_{18}$)alkyl radical, a ($C_4$–$C_{10}$)cycloalkyl radical, a ($C_2$–$C_6$)alkenyl radical, an unsubstituted or substituted ($C_6$–$C_{14}$)aryl or ($C_4$–$C_{12}$)heteroaryl radical containing oxygen, sulfur or nitrogen as a heteroatom or a ($C_7$–$C_{18}$)aralkyl radical and, in the compounds of the formula I where n=2 or 3, a divalent or trivalent radical of a straight-chain or branched, unsubstituted or substituted ($C_1$–$C_{18}$)alkane or cycloalkane, of a mononuclear or polynuclear ($C_6$–$C_{14}$) aromatic or of a ($C_4$–$C_{12}$) heteroaromatic containing oxygen, sulfur or nitrogen as a heteroatom, and n is an integer from 1 to 3 and m is 2 or 3.

4. The radiation-sensitive mixture as claimed in claim 1, wherein the radical $R^2$ is a trifluoromethyl radical.

5. The radiation-sensitive mixture as claimed in claim 1, wherein the radical $R^3$ in the compounds of the formula I where n=1 and in the compounds of the formula II is a ($C_1$–$C_6$)alkyl radical, a cycloalkyl radical, a perfluorinated or highly fluorinated ($C_1$–$C_6$)alkyl radical, a ($C_6$–$C_{10}$)aryl radical, a ($C_7$–$C_{14}$)arylalkyl radical, or a ($C_4$–$C_9$)heteroaryl radical, and, in the compounds of the formula II where n=2, $R^3$ is a ($C_1$–$C_{10}$)alkylene, ethane-1,2-diyl propane-1,3-diyl, ($C_6$–$C_{10}$)arylene, or naphthalenediyl.

6. The radiation-sensitive mixture as claimed in claim 5, wherein the radical $R^3$ has not more than 15 carbon atoms.

7. The radiation-sensitive mixture as claimed in claim 1, wherein the amount of the compound of the formula I and/or II is 0.5 to 25% by weight, based on the total weight of the solids.

8. The radiation-sensitive mixture as claimed in claim 1, wherein the content of the binder is 1 to 95% by weight, based on the total weight of the solids.

9. The radiation-sensitive mixture as claimed in claim 1, wherein the amount of acid-cleavable compounds in the positive-working mixture is 1 to 50% by weight, based on the total weight of the solids.

10. The radiation-sensitive mixture as claimed in claim 1, wherein the content of acid-crosslinkable compounds in the negative-working mixture is 1 to 50% by weight, based on the total weight of the solids.

11. A positive-working or negative-working radiation-sensitive recording material having a substrate and a radiation-sensitive layer, wherein the layer comprises the radiation-sensitive mixture as claimed in claim 1.

12. The radiation-sensitive mixture as claimed in claim 1, wherein the amount of the compound of the formula I and/or II is 1 to 10% by weight, based on the total weight of the solids.

13. The radiation-sensitive mixture as claimed in claim 1, wherein the content of the binder is 5 to 90% by weight, based on the total weight of the solids.

14. The radiation-sensitive mixture as claimed in claim 1, wherein the content of the binder is 30 to 85% by weight, based on the total weight of the solids.

15. The radiation-sensitive mixture as claimed in claim 1, wherein the amount of acid-cleavable compounds in the positive-working mixture is 5 to 40% by weight, based on the total weight of the solids.

16. The radiation-sensitive mixture as claimed in claim 1, wherein the content of acid-crosslinkable compounds in the negative-working mixture is 5 to 40% by weight, based on the total weight of the solids.

17. A sulfonic acid ester of the formula

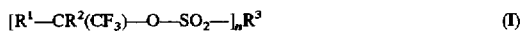  (I)

or

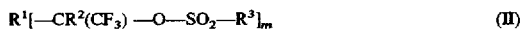  (II)

in which $R^1$ in the compounds of the formula I is a mononuclear or polynuclear unfused or fused ($C_6$–$C_{14}$)aryl or ($C_4$–$C_{11}$) heteroaryl radical containing oxygen, sulfur or nitrogen as a heteroatom and, in the compounds of the formula II, a divalent or trivalent radical of a mononuclear or polynuclear unfused or fused ($C_6$–$C_{14}$)aromatic or ($C_4$–$C_{12}$) heteroaromatic containing oxygen, sulfur or nitrogen as a heteroatom or a divalent radical of the formula —$C_6H_4$—X—$_6H_4$, in which X is an oxygen atom, a carbonyl or sulfonyl group or group $CR^7R^8$, in which $R^7$ and $R^8$ are identical or different and are a methyl or trifluoromethyl radical, $R^2$ is a hydrogen atom or a methyl, trifluoromethyl or cyano radical, $R^3$ in the compounds of the formula I where n=1 and in the compounds of the formula II is a straight-chain or branched, unsubstituted or substituted ($C_1$–$C_{18}$)alkyl radical, a ($C_4$–$C_{10}$)cycloalkyl radical, a ($C_2$–$C_6$)alkenyl radical, an unsubstituted or substituted ($C_6$–$C_{14}$)aryl or ($C_4$–$C_{12}$)heteroaryl radical containing oxygen, sulfur or nitrogen as a heteroatom or a ($C_7$–$C_{18}$)aralkyl radical and, in the compounds of the formula I where n=2 or 3, a divalent or trivalent radical of a straight-chain or branched, unsubstituted or substituted ($C_1$–$C_{18}$)alkane or cycloalkane, of a mononuclear or polynuclear ($C_6$–$C_{14}$) aromatic or of a ($C_4$–$C_{12}$) heteroaromatic containing oxygen, sulfur or nitrogen as a heteroatom, and n and m are each 2 or 3, a sulfonic acid ester of the formula ($F_3C$)$_2$C[$C_6H_4$—($CH_3$)—C($CF_3$)$_2$—O—S$O_2$—$CH_3$]$_2$ being excluded.

* * * * *